United States Patent [19]
Lee et al.

[11] Patent Number: 6,059,726
[45] Date of Patent: May 9, 2000

[54] METHOD FOR LOCATING THE ATRIO-VENTRICULAR (AV) JUNCTION OF THE HEART AND INJECTING ACTIVE SUBSTANCES THEREIN

[75] Inventors: Randall J. Lee, Hillsborough; Michael D. Lesh, Mill Valley, both of Calif.

[73] Assignee: The Regents of the University of California, Oakland, Calif.

[21] Appl. No.: 08/933,915

[22] Filed: Sep. 23, 1997

Related U.S. Application Data

[60] Provisional application No. 60/029,942, Nov. 8, 1996, and provisional application No. 60/029,943, Nov. 8, 1996.

[51] Int. Cl.⁷ .............................. A61B 8/12; A61M 25/01
[52] U.S. Cl. .............................................. 600/439; 604/53
[58] Field of Search ..................................... 600/374, 439, 600/467, 471, 41; 607/119, 122; 604/164, 171, 51–54

[56] References Cited

U.S. PATENT DOCUMENTS

| | | | |
|---|---|---|---|
| 5,074,313 | 12/1991 | Dahl et al. . | |
| 5,103,821 | 4/1992 | King | 600/36 |
| 5,222,501 | 6/1993 | Ideber et al. | 600/439 |
| 5,275,162 | 1/1994 | Edwards et al. | 607/122 |
| 5,324,284 | 6/1994 | Imran . | |
| 5,385,148 | 1/1995 | Lesh et al. | 600/463 |
| 5,409,000 | 4/1995 | Imran . | |
| 5,433,198 | 7/1995 | DeSai | 607/122 |
| 5,490,140 | 2/1996 | Abensour et al. | 370/60.1 |
| 5,496,360 | 3/1996 | Hoffman et al. . | |
| 5,498,238 | 3/1996 | Shapland et al. . | |
| 5,548,589 | 8/1996 | Jeon et al. | 370/60.1 |
| 5,549,603 | 8/1996 | Feiring . | |
| 5,570,355 | 10/1996 | Dail et al. | 370/60.1 |
| 5,609,151 | 3/1997 | Mulier et al. . | |
| 5,661,133 | 8/1997 | Leiden et al. | 514/44 |
| 5,693,622 | 12/1997 | Wolff et al. | 514/44 |
| 5,722,401 | 3/1998 | McGee et al. | 607/122 |

*Primary Examiner*—Francis J. Jaworski
*Attorney, Agent, or Firm*—John P. O'Banion

[57] ABSTRACT

A method for locating the AV junction in the heart and injecting pharmacological or biological compounds into the AV junction for purposes of enhancing or retarding electrical conduction within the AV junction. The AV junction is identified using a combination of echocardiographs and intracardiac electrograms and, once, a catheter with an injection needle and infusion port is positioned into the AV junction for purposes of direct infusion of biologically active compounds to enhance or retard atrioventricular conduction of electrical impulses.

6 Claims, 1 Drawing Sheet

METHOD FOR LOCATING THE ATRIO-VENTRICULAR (AV) JUNCTION OF THE HEART AND INJECTING ACTIVE SUBSTANCES THEREIN

CROSS-REFERENCE TO RELATED APPLICATIONS

This application claims priority from U.S. provisional application Ser. No. 60/029,942 filed on Nov. 8, 1996 and incorporated herein by reference, and from U.S. provisional application Ser. No. 60/029,943 also filed on Nov. 8, 1996 and incorporated herein by reference.

BACKGROUND OF THE INVENTION

1. Field of the Invention

This invention pertains generally to methods for treating inappropriate cardiac conduction, and more particularly to a method for identifying the atrio-ventricular junction in the heart and injecting a pharmacological or biological substance into the junction to enhance or retard conduction of electrical impulses.

2. Description of the Background Art

The cardiac conduction system is responsible for the generation and transmission of the electrical activity that initiates myocardial contraction. Cardiac arrhythmias resulting from electrical conduction disturbances can lead to life threatening ventricular tachyarrhythmias, hemodynamically compromising bradycardias, and heart block.

Within the cardiac conduction system, lies the strategically positioned atrio-ventricular (AV) junction comprising the AV node and the bundle of His. This electrically insulated conduit between the atrium and ventricle synchronizes atrial and ventricular contraction. Perturbations of this strategic cardiac structure produce either (1) rapid transmission of atrial impulses which leads to a rapid ventricular response or (2) heart block which creates atrial and ventricular dissociation.

Tachycardia, which results from enhanced AV conduction, is commonly treated with antiarrhythmic drugs, radiofrequency modification of the AV node, or complete AV junction ablation with the implantation of a permanent pacemaker. Heart block, often a function of the general aging process, is commonly treated by the implantation of a permanent pacemaker. While these current therapies are generally effective in treating the conduction disturbances of the AV junction, their negative aspects include: (1) side effects and proarrhythmias from the antiarrhythmic drugs, (2) irreversible tissue damage caused by radiofrequency modulation/ablation, (3) implantation of a mechanical device and its need for replacement every 5 to 7 years, (4) surgical and mechanical complications resulting from the implantation of the device, (5) negative physical and psychological effects of an implanted mechanical device and (6) a prevalent need to use concurrent antiarrhythmic therapy, radiofrequency modulation/ablation and the implantation of a permanent pacemaker.

Therefore, there is a need for an alternative therapy for treatment of conduction abnormalities that overcomes the negative aspects of current treatment methods. One such approach would be to utilize biologically active substances; for example, cell transplantation or gene therapy. In contrast to the conventional treatment modalities which attempt to simulate the physiological process of the heart, the application of biologically active substances to correct conduction disturbances would enhance the natural physiological processes.

Clearly, organ transplantation has become an accepted method for the replacement of diseased nonfunctional tissue. More recently, however, the use of autologous cellular transplantation for the correction of tissue defects has emerged as a potential therapeutic alternative. For example, healthy chondrocytes have been cultured and transplanted to repair cartilage defects in the knee (Brittberg et al., 1994). Additionally, transplantation of fetal brain cells have been shown to improve certain neurological disorders (Peschanski et al., 1994; Koutouzis et al, 1994).

With the recent demonstration that individual fetal cardiac cells can be successfully transplanted into live adult mice and form the tight bonds within the host heart cells needed for the transplants to contribute to pumping blood (Soonpass et al, 1994), the concept of direct myocardial reconstruction is now a viable option. Independent investigators have begun to explore the utility of fetal myocardial tissue (Leor et al., 1996; Scorsin et al., 1996), genetically modified cardiac myocytes (Gojo et al., 1996; Aoki et al., 1997) and the use of skeletal muscle cell transplantation in the repair of myocardial infracted tissue (Murry et al., 1996).

In the future, patients with severe heart damage may be candidates for cardiac cell transplantation. However, the large amount of transplanted tissue required to augment cardiac mechanical function would not be insignificant. In contrast, the use of cellular transplantation to make significant alterations in cardiac conduction would not require large amounts of grafted tissue. A growing body of evidence suggests that grafted cardiomyocytes (Koh et al., 1993; Soonpaa et al., 1994) do not cause cardiac arrhythmias or negatively influence the host's cardiac rhythm. These observations suggests that the use of grafted cardiac tissue could be utilized as a primary treatment of cardiac conduction disturbances. In addition, the survival of transplanted cells may be enhanced by the inhibition of cell-mediated immunity by the transfer gene products such as transforming growth factor-beta 1 (Qin et al., 1996), interleukin-2 (Gitlitz et al., 1996) and interleukin-10 (Qin et al., 1996).

Genetic identification of the genes responsible for the inherited forms of sudden death (Keating et al), identification of a genetic locus for heart block (Brink et al., 1995) and a familial form of atria fibrillation (Brugada et al, 1997) further enhances the possibility of a molecular genetic approach for the treatment of arrhythmias.

Preclinical studies have already demonstrated the ability to alter cardiac cell physiology with the transfer of sarcoplasmic reticulm calcium ATPase (Hajjar et al., 1997), improve myocardial function following ischemia with angiogenic factors as basic fibroblast growth factor and vascular endothelial growth hormone (Pearlman et al., 1995; Banai et al., 1994; Sellke et al., 1996; Padua R. R.; Sethi R.; Dhalla et al., 1995), enhancement of myocardial function resulting from the over-expression of a beta-adrenergic receptor gene (Milano et al., 1994), alter heart failure with the expression of beta-adrenergic receptors (Ping et al., 1996), and repair myocardial necrosis with muscle growth factors (Murry et al., 1996). Over-expression of a potassium channel by using a replication deficient adenovirus highlights the plausibility to alter cardiac excitability (Johns et al., 1995). In addition, tetracycline-regulation of gene expression is possible which would be useful for gene-transfer based therapies (Fishman et al., 1994).

The field of cardiovascular gene transfer has developed rapidly during the past 5 years (Nable 1995). A recent study has demonstrated that the direct intramyocardial injection of a gene regulating muscle development induced the formation of muscle products in a peri-infarct zone (Murry et al., 1996). This study demonstrates the feasibility for a therapeutic role for gene transfer in myocardial repair. Additionally, in the field of vascular diseases, fervent efforts to provide gene transfer of recombinant DNA and other nucleic acids in blood vessels in vivo has been made to develop new therapeutic strategies for the treatment of vascular diseases.

However, regardless of the specific therapy to be delivered to cardiac tissue, whether cellular components or genetic material, a system must be provided for delivery of these substances into the myocardial matrix. Gene transfer by systemic intravenous administration has been tried, but large doses are required and there is a potential for systemic toxicity since the entire body is exposed to the genetic material. This has led to the development of several local intravascular delivery systems such as the use of vascular stents (Tanguay et al., 1994), coronary artery infusion catheters (Kaplitt et al, 1996), polymer coated angioplasty balloons (Takeshita et al., 1996) or prosthetic grafts for the delivery of gene products. Still, while these devices seem promising in their ability to deliver molecular genetic products to the vascular endothelium, it does not appear possible to use the vascular system to deliver genetic material directly into myocardial tissue, and certainly not any way which will achieve adequate control over the distribution of material to specific anatomic and electrophysiologically determined regions such as the right atrium for the sinus node, the AV junction for control of ventricular rate nor the focus of ventricular tachycardia at the border zone of an infarct in the left ventricle.

Initial experimental studies have demonstrated the feasibility of expressing reporter genes in the myocardium by direct injection of the molecular genetic material (Gal et al., 1993; Kirshenbaum et al., 1993; Guzrnan R. J.; Lemarchand et al., 1993; Kass-Eisler et al., 1993; Barr et al., 1994). The concept that gene therapy can be delivered through a standard hollow needle directly puncturing myocardial tissue has been demonstrated by the use of transthoracic delivery of gene products into the myocardium and by the percutaneous delivery of molecular genetic products (Magovern et al., 1996, Li et al., 1995). These and other studies are exciting because they lend support to the concept of a catheter based delivery system for the employment of molecular genetic products. The limitation of the catheter based delivery systems presently used for the delivery of genetic materials is the inability of these catheters to detect areas of electrical abnormalities within the myocardium. Percutaneous steerable catheter based delivery systems with the ability to measure intracardiac electrograms have been developed for the employment of sclerosing agents such as ethanol. However, these devices also lack the sophistication for the accurate delivery of biologically active substances to specific anatomical structures such as the AV node.

Direct injections of antiarrhythmic agents and sclerosing agents have been injected into the AV node. However, thoracotomies were required. In addition, investigators have employed many techniques to interrupt conduction by damaging specialized muscle along the AV conduction axis (Stanzl et al., 1955). In early studies, complete heart block was produced surgically (Scherlag et al, 1967; Steiner et al., 1968; Shiang et al., 1977; Giannelli et al., 1967;Harrison et al., 1977). Catheter-directed instillation of necrosis-inducing substances, such as ethanol, has also been reported (Wang et al., 1992). More recently, percutaneous vascular access has enabled closed-chest techniques for creation of complete heart block (Fisher et al., 1966; Gallagher et al., 1982).

Traditionally, fluoroscopy in combination with intracardiac electrograms had been used as a method to approximate the general area containing the AV junction. This method is adequate for assessing atrioventricular conduction and/or performing catheter ablation of the AV junction; however, fluoroscopy does not allow the precision to consistently inject substances confined to the AV junction. Therefore, to successfully administer pharmacological or biological substances to the AV junction with the intent of being able to modulate or re-establish AV conduction, a more precise means of identifying the AV junction is required. Accordingly, there is a need for a method of identifying the AV junction and delivering biologically active substances into the AV junction to enhance or retard conduction of electrical impulses. The present invention satisfies those needs, as well as others, and overcomes the deficiencies found in conventional forms of treatment.

BRIEF SUMMARY OF THE INVENTION

The present invention generally comprises a method for locating the AV junction in the heart and injecting pharmacological or biological compounds into the AV junction for purposes of enhancing or retarding electrical conduction within the AV junction. By way of example, and not of limitation, an imaging modality such as echocardiography is combined with intracardiac electrograms to identify the AV junction. The echocardiographs can be transesophageal (TEE), intracardiac (ICE), or transthoracic (TT). Once identified, a catheter with an injection needle and infusion port is positioned into the AV junction for purposes of direct infusion of biologically active compounds (e.g., cells, genes, drugs), either to enhance or retard atrioventricular conduction of electrical impulses.

In accordance with the present invention, a catheter is inserted into a region of tissue adjacent to the atrioventricular junction in the heart. The catheter typically comprises an extendable hollow needle and a reservoir containing a biological compound that is fluidically coupled to the needle. Echocardiography images of the catheter and atrio-ventricular junction are then acquired. Next, intracardiac electrogram signals are acquired from the atrioventricular junction using the catheter as a probe. Then, the catheter is positioned over the atrio-ventricular junction using the echocardiography images in combination with the intracardiac electrogram signals. Once the atrio-ventricular junction is located in this manner, the needle is extended into the atrio-ventricular junction and the biological compound is infused into said junction.

An object of the invention is to accurately identify the location of the AV junction in the heart.

Another object of the invention is to provide a method for treatment inappropriate cardiac conduction.

Another object of the invention is to facilitate injection of pharmacological and biological compounds into the AV junction in the heart.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

Figure 1:
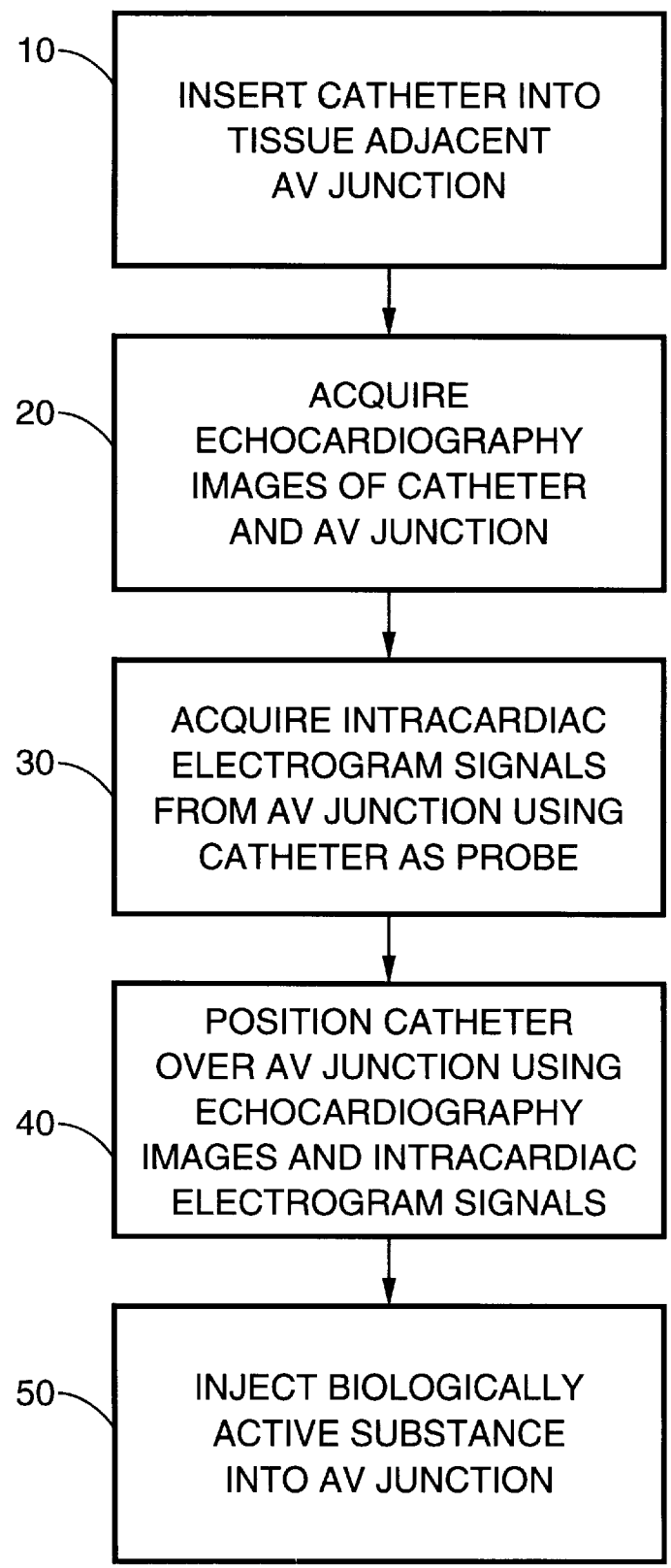
FIG. 1 is a flow diagram of the method of the present invention.

Referring more specifically to the drawings which are presented for illustrative purposes, the present invention is embodied in method generally shown in FIG. 1. It will be appreciated that the method may vary as to the steps and their sequence without departing from the basic concepts as disclosed herein.

In accordance with the present invention, the AV junction is accurately identified by visualizing its anatomical position. The AV junction is located within the triangle of Koch and the His bundle penetrates the ventricular septum at the point where the tendon of Todaro and the tricuspid valve annulus come together (apex of the triangle of Koch). This area of the septum containing the AV junction lies adjacent to the central fibrous body as the specialized conduction tissue travels to the ventricle. The central fibrous body is a dense fibrous structure which the aortic valve, mitral valve and tricuspid valve meet. The AV junction lies posteriorly to the central fibrous body and due to the offsetting of the atrioventricular valves, the specialized muscle appears in closer proximity to the mitral valve than to the tricuspid valve.

Utilizing the basic features of this anatomy which are similar in many species, the AV junction can be identified with sufficient resolution to direct an injection needle into the AV junction for the administration of biologically active substances. This is accomplished by combining conventional echocardiography, such as transesophageal (TEE), intracardiac (ICE) or transthoracic (TT) echocardiography, with intracardiac electrograms for precise location of the AV junction. This combination of imaging, recording of intracardiac electrograms and an injection needle provide the method for the administration of biologically active substances into the AV junction. The use of echocardiography in combination with intracardiac electrograms to identify the AV junction and the injection of substances into the AV junctional region to improve or enhance AV conduction has never been previously attempted, and yields superior results over conventional locating methods.

Referring FIG. 1 which shows the preferred steps undertaken in accordance with the method of the present invention, at step 10 a catheter is inserted into a region of tissue adjacent to the atrio-ventricular junction in the heart. Next, at step 20, echocardiography images of the catheter and atrio-ventricular junction are acquired. At step 30, intracardiac electrogram signals are then acquired from the atrio-ventricular junction using the catheter as a probe. At step 40, the catheter is positioned over the atrio-ventricular junction using the echocardiography images in combination with the intracardiac electrogram signals. Once the atrio-ventricular junction is located in this manner, at step 50 the biologically active substance is infused into the atrio-ventricular junction through the catheter.

It will be appreciated that, once the AV junction is visualized by the imaging modality, the delivery catheter is guided to the AV junction. Correct positioning of the catheter is then confirmed by the characteristic intracardiac electrograms of the AV junction. The injection needle is then advanced and the intracardiac electrograms confirmed before the delivery of biologically active substances. It will also be appreciated that the imaging modality combined with intracardiac electrograms only facilitate use of the intravascular delivery system which can take various forms.

The delivery catheter used in the method described above typically comprises an extendable hollow needle and a reservoir containing a biological compound that is fluidically coupled to the needle. The basic components of this delivery system can include a conventional steerable catheter containing a retractable hollow needle and an ICE catheter. The injection catheter, coupled with the ability to measure intracardiac electrograms from either the tip of the delivery catheter or from the injection needle itself, will greatly enhance the ability to accurately delivery substances within the AV conduction axis. Presently, intracardiac electrograms of the AV junction are generally measured by a multi-electrode catheter (4 electrodes to 8 electrodes) with a spacing between the electrodes of 1 mm to 5 mm. In addition, positioning of the ICE catheter or injection catheter will greatly be facilitated with the development of long sheaths angulated towards the AV conduction axis. It will be appreciated in the context of a delivery system for implementing the method of the present invention that the term "catheter" as used herein generally refers to a probe that also allows for delivery of a biological compound and is not intended as a limitation to a specific type of delivery device.

It will be further appreciated that the delivery catheter could include various forms of energy delivery such as ultrasound, heat, light, etc., to enhance the uptake of the selected compound, in which two sets of bipolar electrodes will be positioned at the tip of the catheter and the tip of the needle. Alternatively, a silver-silver chloride ("MAP") electrode might be employed to assess contact. Also, a piezoelectric crystal near the tip of the infusion catheter can be used as a transponder for localizing the catheter tip during imaging. Such a crystal might also be used as a "range finder" to assess the degree of contact of the needle tip with the tissue to be injected. The catheter can be directed toward the atrioventricular valves with the use of a long guiding sheath.

EXAMPLE 1

We have successfully used intracardiac echocardiography (ICE) (either 6 Fr/12 MHz or 9 Fr/9 MHz Mansfield ICE catheters connected to a Hewlett Packard Sonos 8000) guidance of a hollow needle to successfully inject the AV conduction axis. Injection into the AV junction was accomplished by identifying the mitral and tricuspid valves by intracardiac echocardiography. Once the mitral and tricuspid valves were located, the injection needle was then brought into the same plane as these valves. The needle was directed anteriorly as confirmed with fluoroscopy in the right anterior oblique and left anterior oblique views (angulation of the ICE catheter will also allow assessment of an anterior/posterior position of the injection needle by identifying the aortic valve). Corroboratory evidence that the injection needle was directed towards the AV nodal axis was the ICE images and fluoroscopic demonstration that the injection needle was directed toward a separate catheter placed in the low right atrial septum, which was measuring intracardiac electrograms consistent with HIS electrograms. The intracardiac electrograms of the AV junction (HIS electrograms) were easily identified with respect to its spatial and temporal relationship compared to atrial and ventricular intracardiac electrograms. Once the needle was positioned in the proper position, as defined by intracardiac echocardiography, the needle was advanced. Advancement of the needle into the AV conduction axis produced a junctional beat. In contrast, injection into the ventricular muscle is characterized by a ventricular premature contraction. The anatomical resolution of ICE allows for the visualization of fluid into the AV nodal axis, especially if an abundance of fluid is injected. Gene transfer of beta-galactosidase to the AV node was verified histologically.

This study demonstrated the feasibility of targeting specific anatomical structures within the cardiac conduction system for exogenous gene transfer. The AV node can be specifically injected, allowing for evaluation of the effects of the expression of foreign genes and other biologically active substances on conduction, which may have important implications with regard to future therapeutic applications of this modality. This study also establishes a technique for studying basic properties of electrophysiolgic conduction by modification of ion channel gene expression, and the potential to alter cardiac conduction with gene therapy.

EXAMPLE 2

Via a median sternotomy and guided by superficial landmarks, we injected 100 μl of Ad5/HCMV/LacZ for a total of $4\times10^9$ PFU. To study the effects of adenoviral mediated gene expression on AV nodal electrophysiologic properties, animals were pharmacologically denervated (using atropine and propranolol to inhibit the influence of autonomic nervous system) and studied with right atrial overdrive pacing and atrial programmed extrastimulation, both pre-injection and at the time of sacrifice. Surface ECG PR intervals were measured, together with AV nodal block cycle length (AVBCL) (the rate at which AV conduction becomes sequentially longer, then fails to conduct) and effective refractory period (ERP) (the coupling interval at which an atrial extrastimulus fails to conduct through the AV node). Seven days after injection, the electrophysiology properties were determined, the animals were sacrificed and studied by histochemical staining for β-galactosidase in the area of the AV node.

The AVBCL, ERP, and PR intervals in control animals injected with saline remained unchanged relative to baseline values. AV nodal injections are atraumatic, as evidenced by prompt recovery of nodal conduction properties measured by PR interval, Wenkebach cycle length and AV nodal refractory period (vehicle control animals, n=6; Ad5/HCMV/LacZ, n=5) and the absence of histologic evidence of nodal disruption. Electrophysiologic properties of the AV junction were altered significantly in animals with expression of beta-galactosidase. The mean AVBCL increased by 42+/−16.4 ms (46%, p=0.005) compared to baseline. Similarly, the mean ERP increased by 38+/−8.4 ms (53%, p=0.0008). Interestingly, the PR interval did not change significantly, reflecting the insensitivity of surface EKG markers for cardiac conduction properties. Microscopic evaluation revealed a high rate of infectivity localized to the AV node as assessed by expression of β-galactosidase, accompanied by only moderate inflammation.

This study demonstrates a practical and feasible method for introducing recombinant genes into the atrio-ventricular node of the heart. This model provides a powerful tool for studying basic properties of electrophysiologic conduction by modification of gene expression, and establishes the potential for gene therapy to correct conduction abnormalities and reentrant tachycardias.

Accordingly, it will be seen that this invention provides a precise means of identifying the AV junction and delivering biologically active substances into the AV junction to enhance or retard conduction of electrical impulses. Although the description above contains many specificities, these should not be construed as limiting the scope of the invention but as merely providing illustrations of some of the presently preferred embodiments of this invention. Thus the scope of this invention should be determined by the appended claims and their legal equivalents.

What is claimed is:

1. A high precision method for locating the atrio-ventricular junction in the heart, comprising the steps of:
   (a) inserting a catheter into a region of tissue adjacent to the atrio-ventricular junction in the heart;
   (b) acquiring intracardiac echocardiography images of said catheter and said atrio-ventricular junction;
   (c) acquiring intracardiac electrogram signals from said atrio-ventricular junction using said catheter as a probe; and
   (d) positioning said catheter over said atrio-ventricular junction using said echocardiography images in combination with said intracardiac electrogram signals to locate the atrio-ventricular junction in the heart for injection of a biologically active substance therein to correct conduction disorders.

2. A method for injecting a biological compound into the atrio-ventricular junction in the heart, comprising the steps of:
   (a) inserting a catheter into a region of tissue adjacent to the atrio-ventricular junction in the heart;
   (b) acquiring intracardiac echocardiography images of said catheter and said atrio-ventricular junction;
   (c) acquiring intracardiac electrogram signals from said atrio-ventricular junction using said catheter as a probe;
   (d) positioning said catheter over said atrio-ventricular junction using said echocardiography images in combination with said intracardiac electrogram signals; and
   (e) infusing a biologically active compound into said atrio-ventricular junction through said catheter for correction of conduction disorders.

3. A method as recited in claim 2, wherein said catheter includes an extendable hollow needle and a reservoir containing said biologically active compound fluidically coupled to said needle.

4. A method as recited in claim 2, wherein said biologically active compound alters conduction of electrical impulses in said junction.

5. A method for altering electrical conduction in the atrio-ventricular junction in the heart, comprising the steps of:
   (a) inserting a catheter into a region of tissue adjacent to the atrio-ventricular junction in the heart;
   (b) acquiring intracardiac echocardiography images of said catheter and said atrio-ventricular junction;
   (c) acquiring intracardiac electrogram signals from said atrio-ventricular junction using said catheter as a probe;
   (d) positioning said catheter over said atrio-ventricular junction using said echocardiography images in combination with said intracardiac electrogram signals; and
   (e) infusing a biologically active compound into said atrio-ventricular junction through said catheter, said biologically active compound altering conduction of electrical impulses in said junction.

6. A method as recited in claim 5, wherein said catheter includes an extendable hollow needle and a reservoir containing said biological compound fluidically coupled to said needle.

* * * * *